(12) United States Patent
Haugen et al.

(10) Patent No.: US 9,204,862 B2
(45) Date of Patent: Dec. 8, 2015

(54) METHOD AND APPARATUS FOR PERFORMING ULTRASOUND ELEVATION COMPOUNDING

(75) Inventors: Geir Ultveit Haugen, Oslo (NO); Kjell Kristoffersen, Oslo (NO); Anders R. Sornes, Oslo (NO)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/179,212

(22) Filed: Jul. 8, 2011

(65) Prior Publication Data

US 2013/0012819 A1    Jan. 10, 2013

(51) Int. Cl.
*A61B 8/13* (2006.01)
*A61B 8/08* (2006.01)

(52) U.S. Cl.
CPC .............. *A61B 8/5246* (2013.01); *A61B 8/5269* (2013.01)

(58) Field of Classification Search
CPC combination set(s) only.
See application file for complete search history.

(56) References Cited

U.S. PATENT DOCUMENTS

| | | | |
|---|---|---|---|
| 5,083,568 A * | 1/1992 | Shimazaki et al. | 600/459 |
| 5,546,946 A * | 8/1996 | Souquet | 600/459 |
| 5,608,690 A | 3/1997 | Hossack et al. | |
| 5,655,535 A | 8/1997 | Friemel et al. | |
| 6,117,081 A | 9/2000 | Jago et al. | |
| 6,464,638 B1 | 10/2002 | Adams et al. | |
| 6,511,426 B1 | 1/2003 | Hossack et al. | |
| 6,530,885 B1 | 3/2003 | Entrekin et al. | |
| 6,679,846 B2 | 1/2004 | Napolitano et al. | |
| 6,733,453 B2 | 5/2004 | Freiburger et al. | |
| 6,755,787 B2 | 6/2004 | Hossack et al. | |
| 7,758,509 B2 | 7/2010 | Angelsen et al. | |
| 2001/0023346 A1 | 9/2001 | Loeb | |
| 2005/0049494 A1 | 3/2005 | Gritzky et al. | |
| 2005/0101865 A1 | 5/2005 | Hao et al. | |

OTHER PUBLICATIONS

Krucker, et al., "3-D Compounding of B-Scan Ultrasound Images," University of Michigan, Dept. of Radiology, 137th Meeting of the Acoustical Society of America and 2nd Convention of the European Acoustics Association, Berlin, Mar. 15-19, 1999, 5 pages.

* cited by examiner

*Primary Examiner* — Long V Le
*Assistant Examiner* — Farshad Negarestan
(74) *Attorney, Agent, or Firm* — Dean D. Small; The Small Patent Law Group, LLC

(57) ABSTRACT

A method for generating a spatially compounded image includes acquiring ultrasound information from two or more scan planes, wherein the scan planes are mutually offset by a spatial distance, and wherein at least one of the scan planes is non-planar such that the spatial distance between the scan planes is a function of depth, and combining the information from the scan planes to generate a compounded image. A system and non-transitory computer readable medium are also described herein.

14 Claims, 5 Drawing Sheets

METHOD AND APPARATUS FOR PERFORMING ULTRASOUND ELEVATION COMPOUNDING

BACKGROUND OF THE INVENTION

The subject matter disclosed herein relates generally to ultrasound systems, and more particularly, to methods and systems for performing spatial and elevation compounding using an ultrasound system.

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image. In conventional ultrasound imaging, the image is acquired by a series of scan lines. This results in an image in which some anatomical structures may be "shadowed" by objects closer to the transducer and diagonal structures may not be optimally imaged. Typically, when the boundaries of anatomical structures are parallel to the transducer, the acoustic waves reflect directly back to the transducer with less dispersion and a clear image is obtained. However, diagonal or vertical structures are sub-optimally imaged using conventional ultrasound because of the lower percentage of acoustic energy that reflects back to the transducer. Furthermore, structures that are hidden beneath strong reflectors are also sub-optimally imaged. For example, a small breast cyst may be hidden behind muscular tissue (e.g., tendons), which is a strong superficial reflector.

In addition, another disadvantage of conventional ultrasound imaging is speckle noise. Speckle noise is a result of interference of scattered echo signals reflected from an object, such as an organ. The speckle appears as a granular grayscale pattern on an image. The speckle noise degrades image quality (e.g., speckles obtained from different angles are incoherent) and increases the difficulty of discriminating fine details in images during diagnostic examinations.

At least some known ultrasound systems are capable of spatially compounding a plurality of ultrasound images of a given target into a compound image. The term "compounding" generally refers to non-coherently combining multiple data sets to create a new single data set. The plurality of data sets may each be obtained from imaging the object from different angles, using different imaging properties (such as e.g. aperture, frequency) and/or imaging nearby objects (such as slightly out of the plane steering). These compounding techniques can be used independently or in combination to reduce speckle and improve image quality.

The plurality of data sets or steering frames are combined to generate a single view or compound image by combining the data received from each point in the compound image target that has been received from each compound frame. A transducer array may be utilized to implement electronic beam steering and/or electronic translation of the component frames. The component frames are combined into a compound image by summation, averaging, peak detection, or other combinational means. The compounded image may display relatively lower speckle and better specular reflector delineation than a non-spatially compounded ultrasound image.

BRIEF DESCRIPTION OF THE INVENTION

In one embodiment, a method for generating a spatially compounded image is provided. The method includes acquiring ultrasound image information from a first scan plane, acquiring ultrasound information from a second scan plane where the offset between the scan planes is varied as a function of depth, and combining the information from the first and second scan planes to generate a two-dimensional (2D) compounded image.

In another embodiment, an ultrasound system for generating a spatially compounded image is provided. The system includes an ultrasound probe for transmitting and receiving ultrasound signals to and from an area of interest, a receiver for receiving the ultrasound signals, and a processing unit coupled to the ultrasound probe. The processing unit is programmed to acquire ultrasound image information from a first scan plane, acquire ultrasound information from a second scan plane where the offset between the planes is varied as a function of depth, and combine the information from the first and second scan planes to generate a two-dimensional (2D) compounded image.

In a further embodiment, a non-transitory computer readable medium for generating a spatially compounded image is provided. The computer readable medium is programmed to instruct a processing unit to acquire ultrasound image information from a first scan plane, acquire ultrasound information from a second scan plane where the offset between the planes is varied as a function of depth, and combine the information from the first and second non-linear scan planes to generate a two-dimensional (2D) compounded image.

DETAILED DESCRIPTION OF THE INVENTION

In the following detailed description, reference is made to the accompanying drawings which form a part hereof, and in which is shown by way of illustration specific embodiments in which the present invention may be practiced. It is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel". Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not generated. Therefore, as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Further, the term processor or processing unit, as used herein, refers to any type of processing unit that can carry out the required calculations needed for the invention, such as single or multicore: CPU, Graphics Board, DSP, FPGA or a combination.

Figure 1:
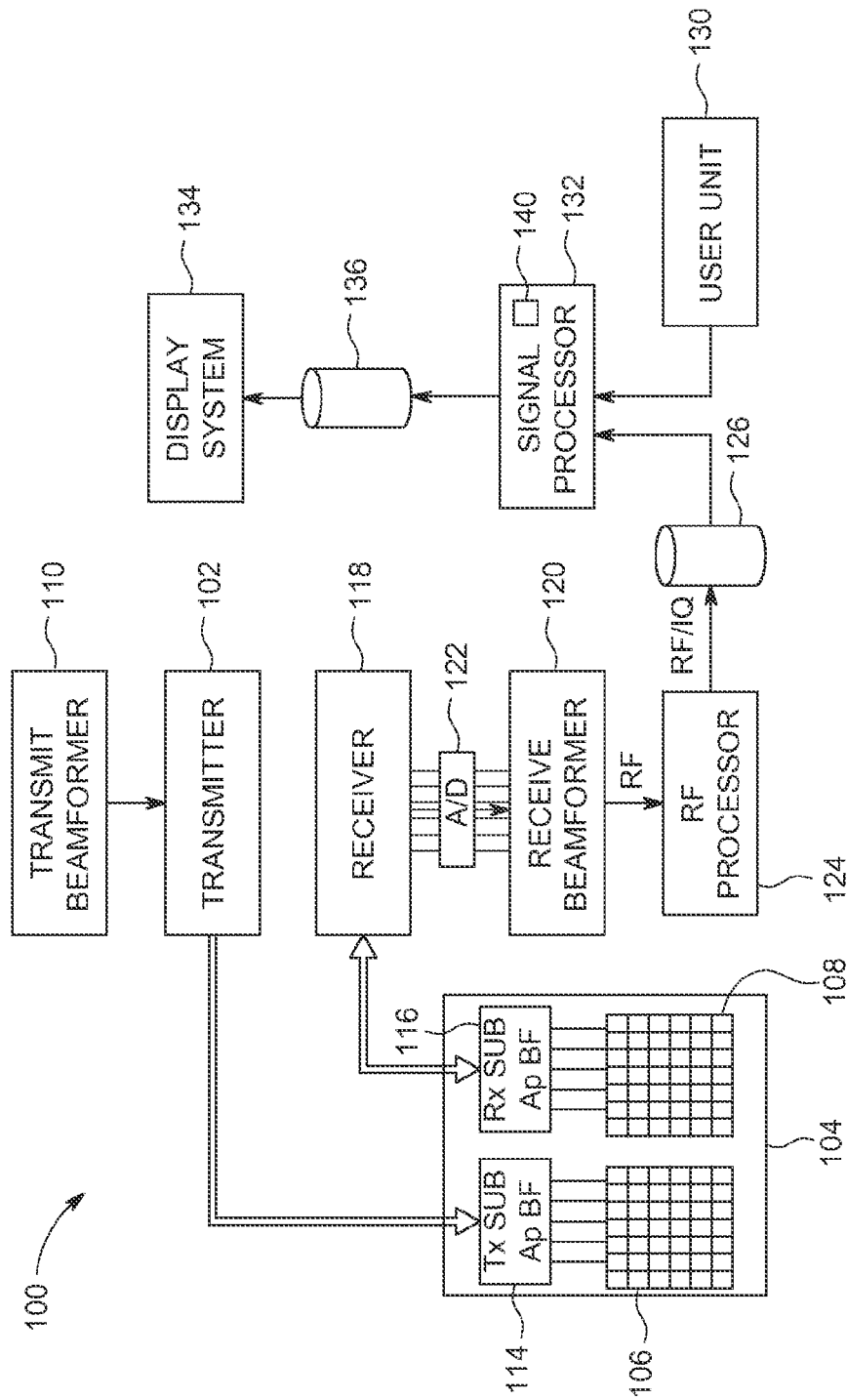
FIG. 1 is a block diagram of an exemplary ultrasound system formed in accordance with various embodiments.

FIG. 1 illustrates a block diagram of an ultrasound system 100 formed in accordance with various embodiments. The ultrasound system 100 includes a transmitter 102 which drives an ultrasound probe 104. The probe 104 may include a 1.75D array, a 2D array and the like. In operation, the probe 104 has the ability to do some degree of steering perpendicular to the scan plane direction. In the exemplary embodiment, the probe 104 is embodied as a two dimensional (2D) array of elements that can steer a beam in the desired spatial direction. The probe 104 includes a transmit group of elements 106 and a receive group of elements 108, that normally constitute the same elements. A transmit beamformer 110 controls the transmitter 102 which, through a transmit sub-aperture beamformer 114, drives the group of transmit elements 106 to emit ultrasonic transmit signals into a region of interest (e.g., human, animal, underground cavity, physical structure and the like). The transmitted ultrasonic signals are back-scattered from structures in the object of interest, like blood cells, to produce echoes which return to the group of receive elements 108. The echoes are received by the receive elements 108 and may include undesirable speckle (e.g., interference caused by scattered echo signals reflected from the region of interest).

The receive group of elements 108 convert the received echoes into analog signals, undergo sub-aperture beamforming by a receive sub-aperture beamformer 116 and are then passed to a receiver 118. The output of the receiver 118 is communicated to a receive beamformer 120, which performs additional beamforming operations and outputs an RF signal. The ultrasound system 100 may include a plurality of A/D converters 122 that are disposed between the receiver 118 and the receive beamformer 120 to illustrate that the incoming received signals may be converted from analog to digital form at the front end of the receive beamformer 120 (such as in analog beamformer).

The receiver 118 and the beamformer 120 maybe combined into a single beamformer which may be digital. The RF signals are then provided to an RF processor 124. The RF processor 124 may include a complex demodulator (not shown) that demodulates the RF signals to form IQ data pairs representative of the echo signals. The RF or IQ signal data may then be routed directly to an RF/IQ buffer 126 for temporary storage. A user input 130 may be used to input patient data, scan parameters, a change of scan mode, and the like. The herein described transmit and receive beam forming is an example and it can be differently distributed between the system part (102, 110, 118, 120, 122, 124) and the probe (104).

The ultrasound system 100 also includes a processing unit 132 to process the acquired ultrasound information (i.e., RF signal data or IQ data pairs) for presentation on a display system 134. The processing unit 132 is adapted to perform one or more processing operations (e.g., compounding) according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 126 during a scanning session and processed in less than real-time in a live or off-line operation.

The ultrasound system 100 may continuously acquire ultrasound information at a frame rate that is suitable for the imaging situation in question. Typical frame rates range from 20-70 but can be lower or higher. The acquired ultrasound information is displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

In the exemplary embodiment, the processing unit 132 may include a spatial compounding module 140. The spatial compounding module 140 is configured to combine a plurality of steering frames corresponding to a plurality of different angles to produce a compound image. The spatial compounding module 140 is configured to control the steering of the ultrasound signals generated by the plurality of transducer elements 106/108 to multiple angles, and may also control the steering of the ultrasound signals generated by the plurality of transducer elements 106/108 to a plurality of angles as discussed in more detail below.

Figure 2:
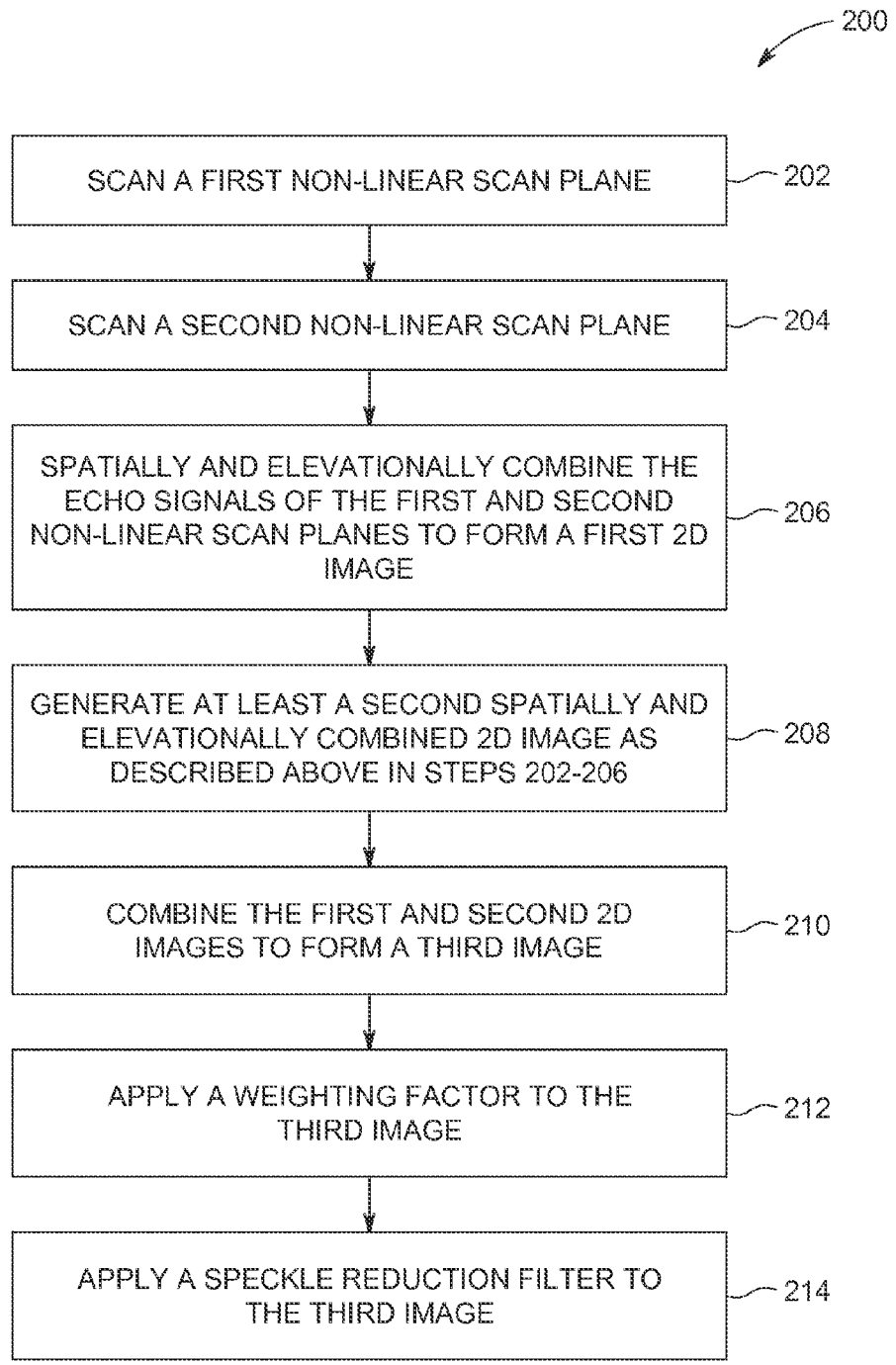
FIG. 2 illustrates a block diagram of an exemplary method of generating an image in accordance with various embodiments.

FIG. 2 is a flowchart of an exemplary method 200 of generating a spatially compounded image using a plurality of images acquired at different imaging planes. Spatial compounding is an imaging technique in which a number of echo signals from a number of adjacent imaging planes are combined. Elevation compounding is discussed in more detail below. The multiple directions help achieve speckle decorrelation. It should be noted that although the method 200 is described in connection with ultrasound imaging having particular characteristics, the various embodiments are not limited to ultrasound imaging or to any particular imaging characteristics.

Figure 4:
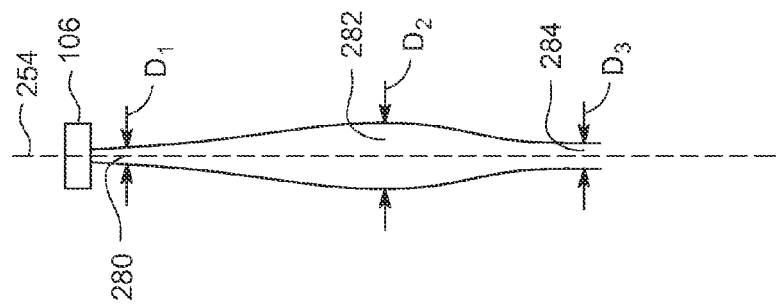
FIG. 4 is a side view of the scan planes shown in FIG. 3.
Figure 3:
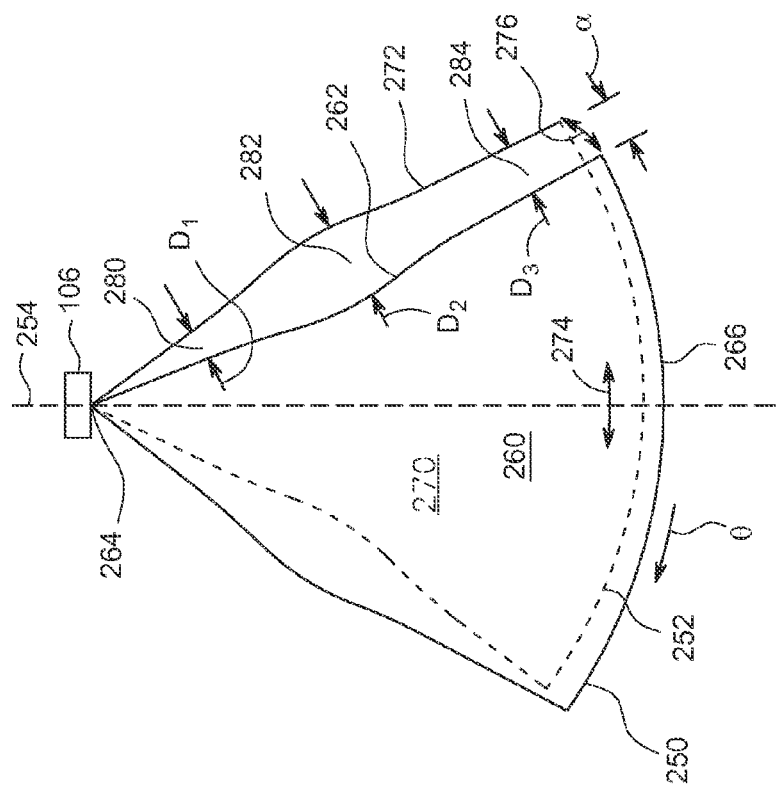
FIG. 3 is an exemplary set of scan planes formed in accordance with various embodiments.

At 202, and also with reference to FIGS. 3 and 4, the probe 104 is utilized to scan a first scan plane 250. In the exemplary embodiment, the scan planes, such as the first scan plane 250, are acquired based on scan parameters that are entered by the operator, from the system, or a combination of the two. The scan parameters may include, for example, a quantity of scan planes to be collected and the degree of spacing between the scan planes as a function of depth. In operation, the scan planes are collected for a thickness, such as from a group or set of adjacent scan planes that are mutually separated by a distance that varies with depth.

In the exemplary embodiment, the probe 104 is utilized to perform a sector scan by scanning the fan-shaped plane 250. The sector scan can have any spatial direction that can be realized with the probe 104. The sector scan scans a region 260 along a direction of the angle θ and along an acoustic beam 262 extending from an emission point 264 to a depth 266, the emission point 264 representing the proximal end of the scan plane and the depth 266 representing the distal end of the scan plane. Beam 262 is drawn as the edge beam of the sector scan, but may represent any beam within the plane 250. Further a scan plane 252 is a sector scan that scans a region 260 along a direction of the angle θ and along an acoustic beam 272 that are drawn as the edge beam of the scan sector, but which may represent any beam within the plane 252. The difference between plane 250 and 252 is that they have an offset in a direction that is mainly perpendicular to the main plane direction and the reference plane 270 which illustrates the result plane from compounding the planes 250 and 252. If the planes 250 and 252 had been planar, e.g. straight two dimensional planes with a fixed angular offset, the result would have been what is known as standard elevation compounding.

In the exemplary embodiment, elevation compounding is improved by optimizing the distance, or angular offset, between the pluralities of planes that are compounded, as a function of depth. This is illustrated for two planes by $D_1$ at 280, $D_2$ at 282 and $D_3$ at 284 that show how the plane spacing may vary as a function of depth. Variation of depth, in this context, means that they are not all identical and they are not related by their depth times a fixed angle between the planes (which would be the case for straight planes with an fixed angular offset). To obtain such a variation in the plane spacing as a function of depth the transmit and/or receive elements 106/108 must be steered to acquire non-straight beams. The planes 250/252 are non-planar as they are built up from the non-straight beams 262/272.

In this exemplary embodiment two mirror symmetrical planes 250/252 are shown. With symmetrical compounding weights the resulting plane 270 will be planar, but this is not a requirement for the scope of various embodiments. In other embodiments three, four, five or more planes can be used. For odd numbers of planes, the center plane is preferably kept planar and other planes are non-planar to realize the mutual distances that vary with depth, but also a non-planar center plane is within the scope of various embodiments.

In the preferred embodiment the adjacent beams in the plurality of adjacent planes are acquired using multiline acquisition. The corresponding beams 262/272 in the adjacent planes 250/252 are acquired with the same shot to increase frame rate. In another embodiment the adjacent planes are acquired independently or a combination of multiline and independent acquisition.

Various embodiments may be used in conjunction with all probes that can do some degree of steering in a direction that is perpendicular to the scan plane. This steering can be realized electronically and/or mechanically. This applies for phased arrays, curved arrays, linear arrays and is independent of the application in question. It can further be used in conjunction with sector scans, curved scans, linear scans, virtual apex scans and any other scan geometry as long as out-of-the plane steering is utilized to acquire the plurality of compound planes.

At 204, the probe 104 is utilized to scan the second scan plane 252. At 206, the images derived at 202 and 204 are spatially combined to form a first 2D or 3D image. In the exemplary embodiment, the second scan plane 252 is also a non-linear scan plane such as the first scan plane 250. The second scan plane 252 is also acquired based on scan parameters that are entered by the operator. The scan parameters may include, for example, a quantity of scan planes to be collected, and/or an angular distance between scan planes. As such, various embodiments can be "repeated" for multiple planes. In a preferred embodiment it is used for each of the planes in multi plane acquisition in 3D. Here a plurality of planes are acquired for a set of spatial directions in space and a plurality of compound planes are acquired for each of these in accordance with the described embodiments. In another embodiment the elevational compounding is used to enhance each of the planes in standard spatial compounding, where each of the planes with different imaging angles are acquired as a plurality of planes in accordance with the described embodiment.

As discussed above, the distance between the elevation planes 300 and 302 is varied with depth to optimize image quality. More specifically, the probe 104 is configured to acquire the acoustic beams 262 such that the resulting scan plane 250 is non-planar due to variable steering respect to the common axis 254. More specifically, while the scan plane 250 is generally fan shaped, the surface of the scan plane 250 is non-planar, between the emission point 264 and the depth 266 of the scan plane 250, referred to herein as the elevation of the scan plane. The acoustic beams 262 may be steered by controlling the shape of the ultrasound signals generated by the transmit and receive elements 106/108. Specifically, the transmit and receive elements 106/108 may be electronically steered at different angles to transmit and receive the non-straight acoustic beams 262.

FIG. 4 is a side view of the first scan plane 250 and the second scan plane 252. In the exemplary embodiment, the spatial and elevation compounding module 140 identifies the thickness, i.e. elevation, of a slice to be created from the scan planes 250 and 252. The slice thickness defines the distance between the scan planes 250 and 252. In the exemplary embodiment, because the planes 250 and 252 are normally non-linear, there is a slight elevational offset between the planes 250 and 252, in a direction 276 that is perpendicular to the main imaging direction of the planes 250 and 252, which is varied in some embodiments. For example, as shown in FIG. 4, the planes 250 and 252 are offset from each other by a distance D1 at an elevation point 280 that is proximate to the emission point 264. The planes 250 and 252 are offset from each other by a distance D2 that is larger than D1, at an elevation point 282 that is midway between the emission point 264 and the point of depth 266. Moreover, the planes 250 and 252 are offset from each other by a distance D3, that is less than D2, at an elevation point 284 that is proximate to the point of depth 266. Accordingly, in some embodiments, the thickness of the slab defined by the planes 250 and 252 diverges from the point 280 to the point 282 and converges from the point 282 to the point 284 such that the planes 250 and 252 are non-planar between the emission point 264 and the depth 266, to enable a thicker, and/or thinner, slab of the region of interest to be used to generate a 2D image.

In the exemplary embodiment, the offset or distance between the planes 250 and 250 are therefore controlled as a function of the depth 266 of the imaging plane which affects the correlation between the acquired images. More specifically, a smaller distance between the planes 250 and 252, such as D1 and D3, provides a relatively high degree of correlation for specular reflectors. The distances D1 and D3 may be for example, on the order of one-half of the beam width to achieve significant speckle decorrelation between the planes 250 and 252. Whereas, a larger distance between the planes 250 and 252, such as D3, provides a lower degree of correlation for speckle and noise. Specifically, correlation of specular reflectors are desired, while speckle and noise should be de-correlated. Accordingly, the offset between the planes 250 and 252 may be tuned to enhance the imaged structures and suppress noise and speckle. In the exemplary embodiment, the beam width is varied as a function of depth to control the spacing between the planes 250 and 252. Moreover, in the case where the vectors of adjacent planes are acquired during a single transmit event, using multiline acquisition (MLA) for example, large spacing facilitates reducing penetration due to reduced overlap between the transmit and receive beams.

Therefore, the planes 250 and 252 may be positioned closer together to regain penetration.

Figure 5:
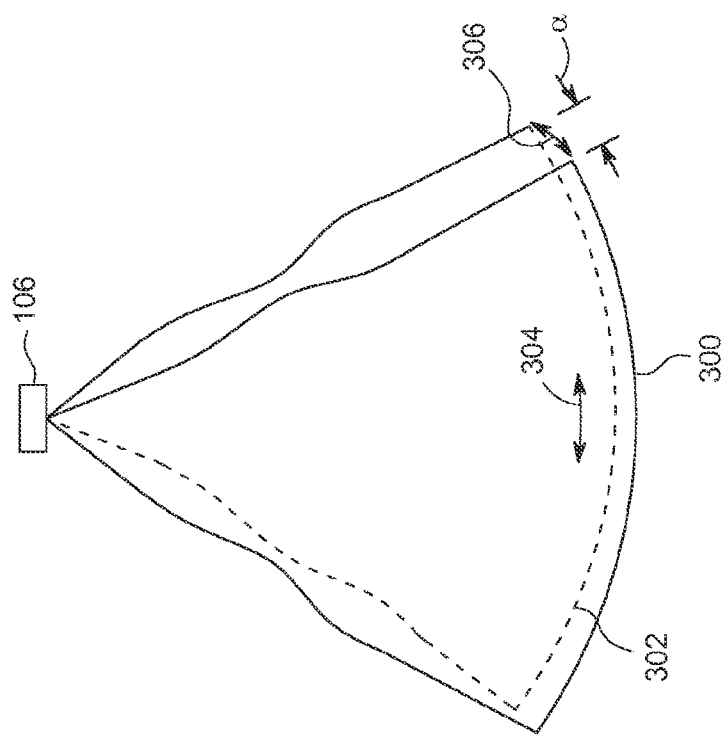
FIG. 5 is another exemplary set of scan planes formed in accordance with various embodiments.

FIG. 5 is another exemplary set of scan planes formed in accordance with various embodiments. In the exemplary embodiment, the offset or distance between the planes 300 and 302 are controlled as a function of the depth of the imaging plane which affects the correlation between the acquired images. The scan parameters also include a spatial offset that defines a spatial distance between two adjacent scan planes, such as scan planes 250 and 252. In the exemplary embodiment, to form the spatial offset the transmit and receive elements 106/108 may be steered at different angles. The first plane 300 is spatially offset from the second plane 302 by an angle α. More specifically, the first plane 300 is scanned at a first angular direction and the second plane 203 is scanned at a second different angle but along a same axis 274. The difference between the angles represents the angle α. It should be realized that although the exemplary embodiment illustrates two scan planes 300 and 302, various embodiments may utilize more than two scan planes to form a spatially compounded image. The sector scan used to scan the planes 300 and 302 may be performed, for example, by steering the receive elements 106 as discussed above. 'When the offset between the compounding planes are controlled as a function of depth and will affect the correlation between the acquired images. Small spacing will give high degree of correlation while large spacing will give lower degree of correlation. Correlations of specular reflectors are desired, while one wants speckle and noise to de-correlate. The spatial offset must be properly tuned to enhance the imaged structures and suppress noise and speckle. Since beam width vary with depth it is important to control the plane spacing as a function of depth to get an optimal result. Further, in the case where the vectors of adjacent planes are acquired during a single transmit event using multiline acquisition, spacing between the beams and/or planes will reduce penetration due to reduced overlap between the transmit beam and the receive beams. In this case one can reduce the offset between the planes to regain penetration.

Figure 6:
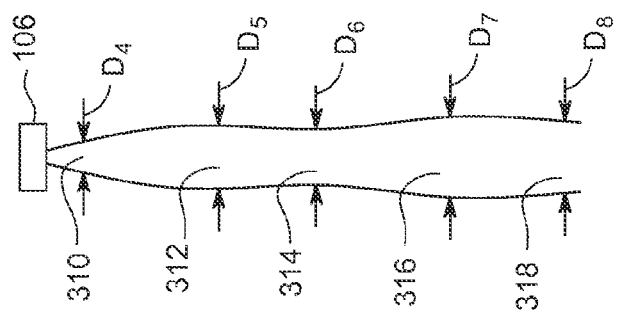
FIG. 6 is a side view of the scan planes shown in FIG. 5.

FIG. 6 is a side view of the scan planes 300 and 302. In the exemplary embodiment, the spatial and elevation compounding module 140 identifies the thickness, i.e. elevation, of a slice to be created from the scan planes 300 and 302. In the exemplary embodiment, because the planes 300 and 302 are non-planar there is a slight elevational offset between the planes 300 and 302, in a direction 306 that is perpendicular to the main imaging direction of the planes 300 and 302. For example, as shown in FIG. 6, the planes 300 and 302 are offset from each other by a distance D4 at an elevation point 310 that is proximate to the emission point 264. The planes 300 and 302 are offset from each other by a distance D5, that is larger than D4, at an elevation point 312. The planes 300 and 302 are offset from each other by a distance D6, that is smaller than D5, at an elevation point 314. The planes 300 and 302 are offset from each other by a distance D7, that is larger than D6, at an elevation point 316. Moreover, the planes 300 and 302 are offset from each other by a distance D8, that is less than D7, at an elevation point 318. Accordingly, in some embodiments, the thickness of the slab defined by the planes 300 and 302 diverges from the point 310 to the point 312, converges from the point 312 to the point 314, converges from the point 314 to 316, and diverges from the point 316 to 318 to enable a thicker slab of the region of interest to be used to generate a 2D image.

The invention, as described herein, can be used for any imaging mode and a combination of imaging modes. The phrase "image" is thus used to refer to an ultrasound mode such as B-mode, CF-mode and/or sub-modes of CF such as TVI, Angio, B-flow, BMI, BMI Angio, and for other embodiments also MM, CM, PW, TVD, CW. Further, for B-mode the invention can be used in conjunction with any B-mode acquisition methods such as harmonic imaging, contrast imaging, pulse inversion, power modulation and coded excitation.

In the exemplary embodiment, the compounding of the plurality of planes can be done with fixed weights. In other embodiments one can use adaptive weights (for example based on a quality measure or image analysis) and/or on transformed data.

Referring again to FIG. 2, at 208, the ultrasound system 100 generates at least a second spatially and elevationally combined 2D image as described above in steps 202-206. In the exemplary embodiment, the ultrasound system 100 may acquire a series of spatially and elevationally combined 2D images using a multiplane acquisition scanning technique. More specifically, multiplane acquisition may be embodied as a biplane, a tri-plane, or N-plane scan that is specified by the user. The system 100 sets the angles, orientation, tilt, and the like for a given type of multiplane scan for the planes with respect to one another based on predefined default values or the user entered parameter values. For example, if the user designates bi-plane imaging, the user may then set parameter values for the angles of the planes to be 0 degrees and 90 degrees with respect to a base reference plane. Optionally, if the user designates tri-plane imaging, the user may then set parameter values for the angles of the planes to be 0 degrees, 60 degrees and 120 degrees with respect to a base reference plane.

Figure 7:
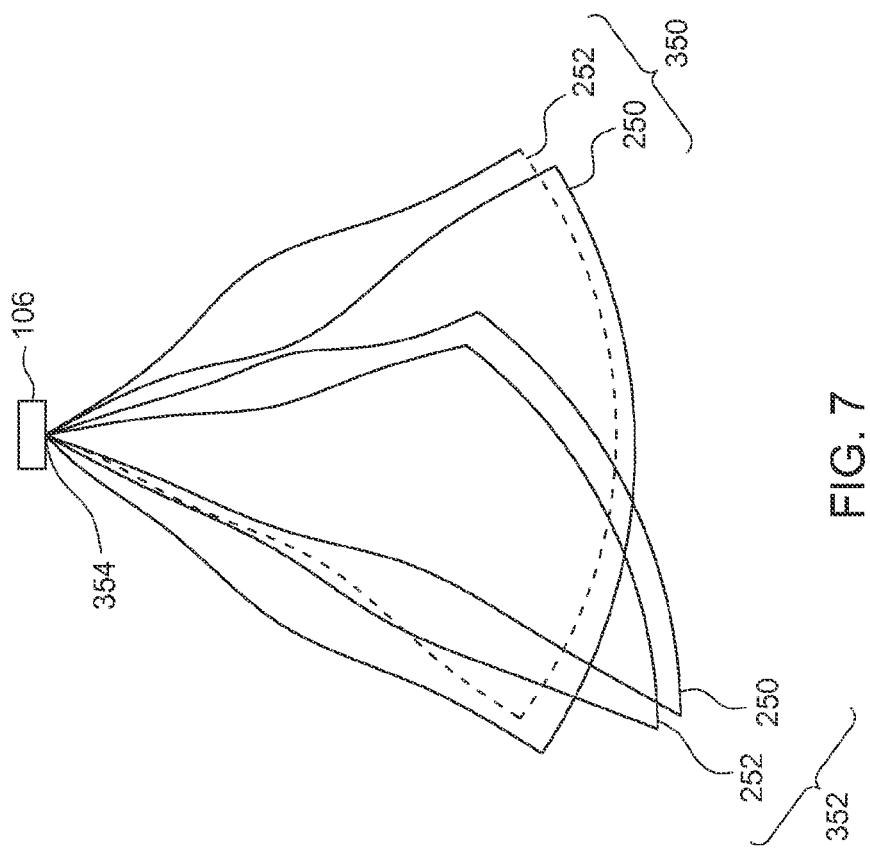
FIG. 7 illustrates a plurality of exemplary scan planes formed in accordance with various embodiments.

For example, FIG. 7 illustrates a multi-plane image acquisition that may be performed by the imaging system 100. In the exemplary embodiment, the multi-plane image data shown in FIG. 7 includes two, sets of the scan planes 250 and 252 described above. However, it should be realized that the multi-plane image data may include two or more sets of the scan planes 250 and 252, two or more sets of the scan planes 300 and 302, or two or more sets of any scan planes having a non-linear elevational profile. The multi-plane image data may be obtained from a current image scan or from previously obtained and stored data. In the exemplary embodiment, the multi-plane image data is acquired from a 3D ultrasound scan using two or more image planes. For example, as shown in FIG. 7, the image data may be obtained from a bi-plane image scan using two-planes 250 and 252. In another embodiment, the image data may be obtained from a tri-plane image scan using three-planes (not shown). It should be noted that each of the scan planes 250 and 252 is a 2D scan plane. Additionally, it should be noted that the multi-plane image acquisition may be performed using any type of ultrasound probe and/or ultrasound imaging system as appropriate.

In some embodiments, such as in a bi-plane image acquisition implementation, the ultrasound information is acquired substantially simultaneously or consecutively within a short period of time (e.g. 1/20 second) for the two differently oriented scan planes 250 and 252 or views. It should be noted that the spacing (e.g., angular rotation) between a first set 350 of scan planes 250 and 252 and a second set 352 of scan planes 250 and 252 may be the same or varied. For example, one data slice associated with the first set 350 of scan planes may correspond to an angle of 0 degrees, another data slice associated with the second set of scan planes 352 may correspond to an angle of 60 degrees, and a third set of scan planes (not shown) may correspond to an angle of 120 degrees, etc.

At 210, a 2D combined image, a 3D combined image or other image may be formed from the image planes (e.g., individual planes of a multi-plane dataset). The sets of scan planes 350 and 352 may intersect at a common rotational axis 354 or, alternatively, intersect at different axes. Two slice images (e.g., 2D slices cut through a full volume 3D dataset) may be generated by image data acquired at the two sets of scan plane 350 and 352, which are two views of the scan object at about the same point in time due to simultaneous acquisition of the scan data for the two sets of scan planes 350 and 352. The two slice images may be, for example, of a patient's heart at a specific point in time of the heart beat or cycle. Alternatively, the three slice images may show continuous motion of a patient's heart while the heart beats. It should be noted that one or more of the sets of scan planes 350 and 352 may be tilted relative to a scanning surface of the ultrasound probe 104 (shown in FIG. 1). Additionally, the angular rotation between the sets of scan planes 350 and 352 may be changed or varied. It also should be noted that the sets of scan planes 350 and 352 may be acquired by mechanical or electronic steering of the ultrasound probe 104. For example, in some embodiments, the ultrasound probe may include electronic steering means as is known that electronically steers a matrix array, as shown in FIG. 1, to acquire the image data corresponding to the sets of scan planes 350 and 352. In another embodiment, the ultrasound probe 104 may include a mechanically movable scan head as is known that moves the array of elements 106/108 (shown in FIG. 1) to acquire image data (e.g., image planes) corresponding to the sets of scan planes 350 and 352. In still other embodiments, a combination of mechanical and electronic steering as is known may be used. It should be noted that during acquisition of the sets of scan planes 350 and 352, the probe housing in various embodiments is not moved relative to the object being examined.

It also should be noted that more than two scan planes may be used to acquire image information. For example, three, four, five, six images (e.g., six image planes) may be generated at the six planes, which may be located, for example, equidistance from each other. However, the angular spacing between each of the scan planes may be varied. Accordingly, the number of apical planes may be increased using, for example, sequentially acquired multi-plane scan data by electronically rotating the scan angles. In some embodiments, multiple tri-plane acquisitions may be performed that are angularly rotated with respect to each other or a single acquisition having more than three scan planes may be performed. Thus, increased image resolution of, for example, the left ventricle of an imaged heart may be provided.

In the exemplary embodiment, at 212, a weighting factor may be applied to the image formed at 210. In the exemplary embodiment, relative weights are assigned to the areas where the planes overlap and do not overlap. For example, the same weighting factor may be applied to areas that overlap. Optionally, different weights may be assigned to each of the areas that do not overlap. By weighting the acquired scan data differently, speckle interference may be decreased, thereby improving image quality. In addition, weighting eliminates any detected motion prior to combining the plurality of steering frames into a compound image. Optionally, different levels of compounding may be used. For example, a high level of compounding (e.g., five or more image frames steered at large angles) may be used. Optionally, other applications may require no compounding or a lower level of compounding (e.g., three frame images and transducer elements steered at smaller angles). Therefore, in an embodiment, a plurality of default preset choices for different levels of compounding may be provided (e.g., no compounding, low compounding, high compounding).

In addition, the ultrasound system 100 provides for reducing interference caused by speckle noise. Speckle noise is an intrinsic property of ultrasound imaging, the existence of speckle noise in ultrasound imaging reduces image contrast and resolution. Accordingly at 214, a speckle reduction filter is used to reduce speckle noise. The speckle reduction filter usually does not create motion artifacts, preserves acoustic shadowing, and enhancement. However, the speckle reduction filter may cause a loss of spatial resolution and reduce processing power of an ultrasound imaging system.

A speckle reduction filter (not shown), such as a low pass filter, may be utilized to reduce speckle noise in an image generated the ultrasound system 100. An example of a low pass filter is a finite impulse response (FIR) filter. In an alternative embodiment, the speckle reduction filter is a mathematical algorithm that is executed by the processor 132 and that is used on a single image frame to identify and reduce speckle noise content. In yet another embodiment, the speckle reduction filter is a median filter, a Wiener filter, an anisotropic diffusion filter, or a wavelet transformation filter, which are mathematical algorithms executed by the processor 132. In still another alternative embodiment, the speckle reduction filter is a high pass filter that performs structural and feature enhancement. An example of a high pass filter is an infinite impulse response (IIR) filter. In the median filter, a pixel value of an image generated using the ultrasound system 100 is replaced by a median value of neighboring pixels. The Wiener filter can be implemented using a least mean square (LMS) algorithm. The anisotropic diffusion filter uses heat diffusion equation and finite elements schemes. The wavelet transformation filter decomposes echo signals into a wavelet domain and obtained wavelet coefficients are soft-thresholded. In the soft-thresholding, wavelets with absolute values below a certain threshold are replaced by zero, while those above the threshold are modified by shrinking them towards zero. A modification of the soft thresholding is to apply non-linear soft thresholding within finer levels of scales to suppress speckle noise.

A technical effect of at least one embodiment is to utilize a spatial compounding technique to improve imaging by averaging different ultrasound images of different targets. The averaging is done to improve imaging of specular reflectors and to reduce speckle and noise in the resulting image. Additionally, the spatial compounding is done in combination with variable spacing (or angle) between the planes as a function of depth, referred to herein as elevation compounding. More specifically, when the spacing between planes is varied as a function of depth, the planes that are averaged are not planar any more. The control of the spacing allows optimization of the tradeoff between the overall thickness of the slice (determined by the region spanned by the planes), the degree of decorrelation of speckle and noise between the planes, and the degree of penetration at large depths for planes that are acquired as multi-line acquisitions (MLAs) for the same shot.

In some embodiments, the spacing between planes is controlled as a function of the beamwidth of the ultrasound probe such that less spacing may be used when the beamwidth is narrow, or if the vectors of adjacent planes are acquired from the same transmit event, using for example, parallel beamforming.

Thus, in various embodiments, the compounding described herein is based on planes with a slight spatial offset that is accurately controlled to optimize the quality of the resulting image. An offset on the order of one-half of the slice thickness is required, in some embodiments, to obtain significant speckle decorrelation between adjacent planes. Various embodiments, combine two or more ultrasound sector scans with a slight offset in a direction that is perpendicular to the main imaging direction of the planes. In this manner, information from a thicker slab of the imaging object is combined.

It should be noted that although the various embodiments may be described in connection with an ultrasound system, the methods and systems described herein are not limited to ultrasound imaging or a particular configuration thereof. For example, the various embodiments may be implemented in other non-medical imaging systems, for example, non-destructive testing systems.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using micro controllers, reduced instruction set computers (RISC), graphics board, application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for acquiring imaging information comprising:
    transmitting plural non-straight acoustic beams from at least one emission point in a depth direction extending away from the at least one emission point;
    acquiring, with plural receive elements, a first non-planar scan plane of reflections of the acoustic beams, wherein the non-planar scan plane is curved in an elevation direction as the non-planar scan plane extends along the depth direction, wherein the elevation direction is perpendicular to a main imaging direction of the scan plane, and wherein the receive elements are arranged in a 2D array extending at least along the elevation direction;
    acquiring at least a second scan plane, wherein the non-planar scan plane and the at least a second scan plane are mutually offset by a distance in the elevation direction that varies along the depth, wherein the at least a second scan plane is non-planar and curved in the elevation direction as the at least a second scan plane extends along the depth direction; and
    combining information from the first non-planar scan plane and the at least a second scan plane to generate a compounded image.

2. The method of claim 1, further comprising steering the plural receive elements in a direction generally perpendicular to the first scan plane.

3. The method of claim 1, wherein the non-planar scan planes define fan shapes, wherein the elevation direction is generally perpendicular to the fan shapes.

4. The method of claim 1, wherein the receive elements are configured as transmit and receive elements configured to transmit the acoustic beams and to receive the reflections, the method further comprising steering the transmit and receive elements at different angles when transmitting and receiving.

5. The method of claim 1, wherein the non-planar scan planes are acquired using multiline acquisition.

6. An ultrasound system comprising:
an ultrasound probe configured to transmit and receive ultrasound signals to and from an area of interest, the ultrasound probe configured to transmit plural non-straight acoustic beams from at least one emission point in a depth direction extending away from the at least one emission point, the ultrasound probe comprising plural receive elements configured to acquire reflections of the plural acoustic beams, wherein the receive elements are arranged in a 2D array extending at least along the elevation direction; and
one or more processors coupled to the ultrasound probe, the one or more processors configured to:
acquire, using the plural receive elements, a first non-planar scan plane of the reflections, wherein the non-planar scan plane is curved in an elevation direction as the non-planar scan plane extends along the depth direction, wherein the elevation direction is perpendicular to a main imaging direction of the scan plane;
acquire at least a second scan plane, wherein the non-planar scan plane and the at least a second scan plane are mutually offset by a distance in the elevation direction that varies along the depth, wherein the at least a second scan plane is non-planar and curved in the elevation direction as the at least a second scan plane extends along the depth direction; and
combine information from the first non-planar scan plane and the at least a second scan plane to generate a compounded image.

7. The system of claim 6, wherein the one or more processors are further configured to steer the receive elements in a direction generally perpendicular to the first scan plane.

8. The system of claim 6, wherein the non-planar scan planes define fan shapes, wherein the elevation direction is generally perpendicular to the fan shapes.

9. The system of claim 6, wherein the receive elements are configured as transmit and receive elements configured to transmit the acoustic beams and to receive the reflections, and wherein the one or more processors are configured to steer the transmit and receive elements at a different angle when receiving the reflections from an angle used when transmitting the acoustic beams.

10. The system of claim 6, wherein the one or more processors are configured to acquire the non-planar scan planes using multiline acquisition.

11. A tangible and non-transitory computer readable medium comprising one or more computer software modules configured to direct one or more processors to:
transmit plural non-straight acoustic beams from at least one emission point in a depth direction extending away from the at least one emission point;
acquire, via plural receive elements, a first non-planar scan plane of reflections of the acoustic beams, wherein the non-planar scan plane is curved in an elevation direction as the non-planar scan plane extends along the depth direction, wherein the elevation direction is perpendicular to a main imaging direction of the scan plane, wherein the receive elements are arranged in a 2D array extending at least along the elevation direction;
acquire at least a second scan plane, wherein the non-planar scan plane and the at least a second scan plane are mutually offset by a distance in the elevation direction that varies along the depth, wherein the at least a second scan plane is non-planar and curved in the elevation direction as the at least a second scan plane extends along the depth direction; and
combine information from the first non-planar scan plane and the at least a second scan plane to generate a compounded image.

12. The tangible and non-transitory computer readable medium of claim 11, wherein the computer readable medium is further configured to steer the plural receive elements in a direction generally perpendicular to the first scan plane.

13. The tangible and non-transitory computer readable medium of claim 11, wherein the receive elements are configured as transmit and receive elements configured to transmit the acoustic beams and to receive the reflections, wherein the computer readable medium is further configured to steer the transmit and receive elements at different angles when transmitting and receiving.

14. The tangible and non-transitory computer readable medium of claim 11, wherein the non-planar scan planes define fan shapes, wherein the elevation direction is generally perpendicular to the fan shapes.

* * * * *